United States Patent

Slater et al.

[11] Patent Number: 6,041,679
[45] Date of Patent: Mar. 28, 2000

[54] ENDOSCOPIC END EFFECTORS CONSTRUCTED FROM A COMBINATION OF CONDUCTIVE AND NON-CONDUCTIVE MATERIALS AND USEFUL FOR SELECTIVE ENDOSCOPIC CAUTERY

[75] Inventors: Charles R. Slater, Fort Lauderdale; Matthew A. Palmer, Miami; Peter Kratsch, Sunrise, all of Fla.

[73] Assignee: Symbiosis Corporation, Miami, Fla.

[21] Appl. No.: 08/308,983

[22] Filed: Sep. 19, 1994

Related U.S. Application Data

[63] Continuation of application No. 08/107,454, Aug. 17, 1993, Pat. No. 5,396,900, which is a continuation-in-part of application No. 07/922,023, Jul. 28, 1992, Pat. No. 5,331,971, which is a continuation of application No. 07/680,392, Apr. 4, 1991, Pat. No. 5,192,298, and a continuation-in-part of application No. 07/978,249, Nov. 18, 1992, Pat. No. 5,395,375, and a continuation-in-part of application No. 08/016,595, Feb. 11, 1993, abandoned.

[51] Int. Cl.⁷ ..................................................... B21K 11/02
[52] U.S. Cl. ........................... 76/104.1; 30/140; 164/517; 606/170
[58] Field of Search ................................ 76/101.1, 104.1; 30/140; 606/43–48, 170, 171; 164/516–518

[56] References Cited

U.S. PATENT DOCUMENTS

| | | | |
|---|---|---|---|
| 1,071,978 | 9/1913 | White . | |
| 3,100,489 | 8/1963 | Bagley | 128/303.17 |
| 3,153,826 | 10/1964 | Horton | 164/517 |
| 3,460,539 | 8/1969 | Anhalt, Sr. | 128/303.17 |
| 3,895,636 | 7/1975 | Schmidt | 128/305 |
| 3,920,021 | 11/1975 | Hiltebrandt | 128/303.17 |
| 3,924,608 | 12/1975 | Mitsui | 128/2 B |
| 3,987,795 | 10/1976 | Morrison | 128/303.14 |
| 4,074,718 | 2/1978 | Morrison, Jr. | 128/303.14 |
| 4,231,371 | 11/1980 | Lipp | 30/140 |
| 4,232,676 | 11/1980 | Herczog | 128/303.14 |
| 4,401,952 | 8/1983 | Basawapatna | 330/277 |
| 4,418,692 | 12/1983 | Guay | 128/303.14 |
| 4,622,966 | 11/1986 | Beard | 128/303.14 |
| 4,674,498 | 6/1987 | Stasz | 128/303.14 |
| 4,681,105 | 7/1987 | Tritt | 128/303.17 |
| 4,685,459 | 8/1987 | Koch et al. | 128/303.17 |
| 4,763,669 | 8/1988 | Jaeger | 128/751 |
| 4,802,476 | 2/1989 | Noerenberg et al. | 128/303.14 |
| 4,850,353 | 7/1989 | Stasz et al. | 128/303.14 |
| 4,862,890 | 9/1989 | Stasz et al. | 128/303.14 |
| 4,958,539 | 9/1990 | Stasz et al. | 76/104.1 |
| 5,007,908 | 4/1991 | Rydell | 606/47 |
| 5,013,312 | 5/1991 | Parins et al. | 606/37 |

(List continued on next page.)

FOREIGN PATENT DOCUMENTS

| | | | |
|---|---|---|---|
| 517244 | 12/1992 | European Pat. Off. | A61B 17/39 |
| 518230 | 12/1992 | European Pat. Off. | A61B 17/39 |

*Primary Examiner*—Douglas D. Watts
*Attorney, Agent, or Firm*—Finnegan, Henderson, Farabow, Garrett & Dunner, L.L.P.

[57] ABSTRACT

A non-metallic end effector for use in an endoscopic surgical tool includes a metallic core for strength and for providing a selected electrode surface on the end effector. Selectively conductive end effectors are manufactured by insert molding a plastic or ceramic or other non-conductive body around a metallic or otherwise conductive core. The conductive core is exposed on a selected portion of the working surface of the end effector and extends through the non-conductive body of the end effector for coupling to an electrical source. Selectively conductive end effectors of this type can also be manufactured by coating a cast end effector member with a non-conductive polymer or by metallically plating a non-conductive ceramic end effector member. By extending the conductive core of a selectively conductive end effector member to the pivot hole of the member, electrical coupling can be made through the clevis and tube of an endoscopic instrument. By extending the conductive core to the actuation bore of an end effector member, electrical coupling can be made through the push rod or other actuation member in an endoscopic instrument. Using both techniques, a bipolar selective cautery end effector can be provided on an endoscopic instrument.

9 Claims, 6 Drawing Sheets

U.S. PATENT DOCUMENTS

| | | | |
|---|---|---|---|
| 5,049,148 | 9/1991 | Mehl | 606/43 |
| 5,077,506 | 12/1991 | Krause | 318/71 |
| 5,085,659 | 2/1992 | Rydell | 606/47 |
| 5,104,394 | 4/1992 | Knoepfler | 606/143 |
| 5,151,102 | 9/1992 | Kamiyama et al. | 606/51 |
| 5,217,458 | 6/1993 | Parins | 606/48 |
| 5,219,357 | 6/1993 | Honkanen et al. | 606/205 |
| 5,309,640 | 5/1994 | Caron | 30/140 |

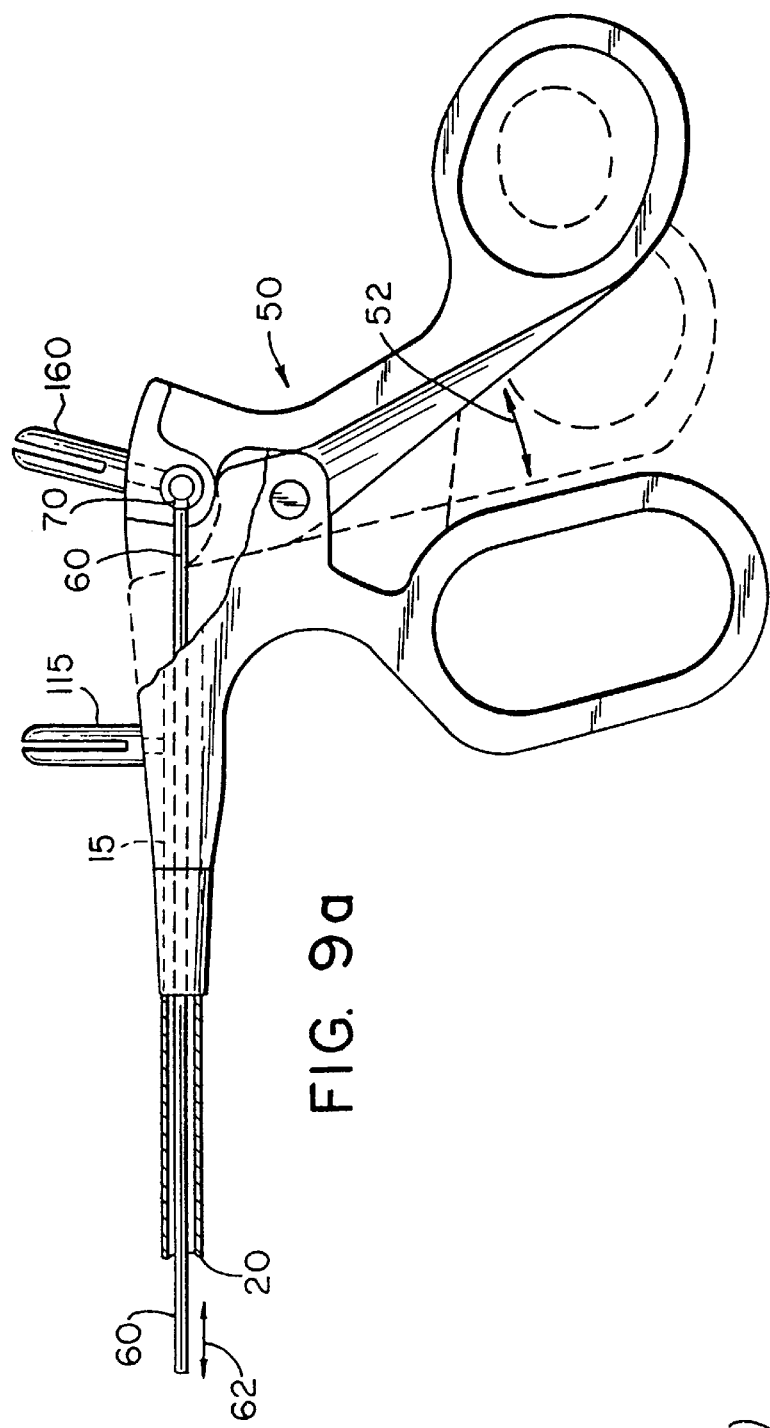
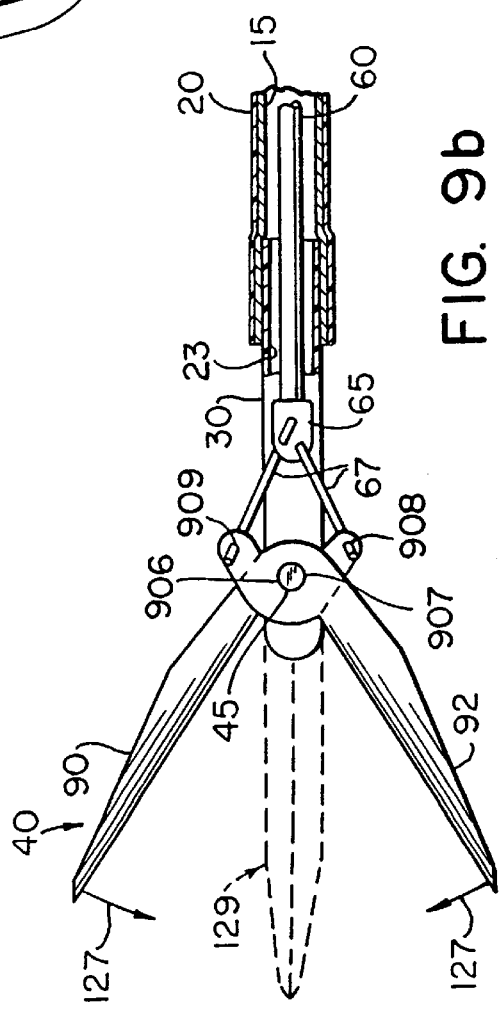
FIG. 9a
FIG. 9b

ENDOSCOPIC END EFFECTORS CONSTRUCTED FROM A COMBINATION OF CONDUCTIVE AND NON-CONDUCTIVE MATERIALS AND USEFUL FOR SELECTIVE ENDOSCOPIC CAUTERY

This application is a continuation of Ser. No. 08/107,454, now U.S. Pat. No. 5,396,900 which in turn is a continuation-in-part of Ser. Nos. 07/922,023 now U.S. Pat. No. 5,331,971 (which is a continuation of Ser. No. 07/680,392 now issued as U.S. Pat. No. 5,192,298), U.S. Ser. No. 07/978,249 now U.S. Pat. No. 5,395,375 entitled "Arthroscopic Surgical Instruments", and U.S. Ser. No. 08/016,595 now abandoned entitled "Endoscopic Biopsy Forceps Devices with Selective Bipolar Cautery", which are hereby incorporated by reference herein in their entireties.

BACKGROUND OF THE INVENTION

This invention relates to endoscopic surgical devices. More particularly, the invention relates to an endoscopic surgical tool having end effectors made out of a combination of plastic or ceramic and metal and useful for selective endoscopic cautery.

Endoscopic surgery is widely practiced throughout the world today and its acceptance is growing rapidly. In general, endoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like. Because of their very small size and the requirements of strength and/or sharpness, end effectors are difficult to manufacture and are typically formed of forged stainless steel. As such, they form an expensive portion of the endoscopic instrument.

Modern endoscopic procedures often involve the use of electrocautery. Indeed, several types of electrocautery devices for use in endoscopic surgery are described in the prior art. U.S. Pat. No. 4,418,692 to Guay, for example, discloses a device for use in laparoscopic tubal cauterization for blocking the Fallopian tubes of a patient. The device comprises a substantially tubular body member having a spring-biased piston slidably mounted therein. A pair of electrodes (either monopolar or bipolar) are disposed to grasp living tissue when the piston is in a first position biased by the spring and to release the tissue when a button is pressed which moves the piston into a second position. The device includes a circuit breaker which interrupts current flowing to the electrodes when the piston is in the second position. When the electrodes grasp the tissue, however, current is supplied to the entire surface of the electrode, that is, both the grasping surface and the outer non-grasping surface.

Another electrosurgical instrument for use in combination with an endoscope is disclosed in U.S. Pat. No. 5,007,908 to Rydell for "Electrosurgical Instrument Having Needle Cutting Electrode and Spot-Coag Electrode". Rydell's device includes an elongated flexible tubular member with a plurality of lumens. The distal end of the tubular member is provided with a bullet shaped ceramic tip covered with a conductive layer and having an opening coupled to a first one of the lumens. The conductive layer is coupled to a conductor which extends through a second one of the lumens to an electrical source. A second conductor, also coupled to the electrical source is slidable through the first lumen by a plunger. The two electrodes form a bipolar pair. In a second embodiment, the conductive layer on the ceramic tip is split by an insulating gap and both halves of the tip form a bipolar pair of electrodes. As with the Guay device, above, substantially the entire distal surface of Rydell's device serves as an electrode when energized.

Other electrocautery probes for use with an endoscope are disclosed in U.S. Pat. No. 3,920,021 to Hiltebrandt. Hiltebrandt discloses several types of probes similar to Rydell's in that they have a substantially bullet shaped tip with hemispheric or annular conductors forming electrode pairs. Hiltebrandt also shows electrodes similar to Guay's; a pair of springy arms slidable through a tube member to grasp and release tissue. Of course, the gripping force obtainable by either Guay's or Hiltebrandt probes is severely limited because the electrodes must be "springy".

It is known in electrosurgery to insulate a portion of the surface area of an electrode so that only a precise or at least well defined portion of an electrode's surface is conductive. This is desirable in order to protect both the surgeon and the tissue adjacent to the site of electrosurgery from accidental cautery by an electrode having a broad fully conductive surface. U.S. Pat. No. 3,100,489 to Bagley, for example, shows cautery forceps where the entire surface of the forceps with the exception of the forceps tips is provided with an overall pliable insulating coating of rubber or synthetic rubber-like material. U.S. Pat. No. 5,049,148 to Mehl discloses a "Radio Frequency Hair Removal Tweezer" which includes insulated tweezer arms with conducting pads at the tips of the arms so that RF energy can be applied to individual hairs without burning surrounding skin through arcing. Nevertheless, it is heretofore unknown to selectively insulate portions of an endoscopic end effector to provide a well defined and discrete electrosurgical surface. It is also heretofore unknown to make endoscopic end effectors primarily from plastic, as plastic is typically considered too weak to properly serve desired functions.

SUMMARY OF THE INVENTION

It is therefore an object of the invention to provide an endoscopic surgical instrument with a cauterizing end effector where only a part of the surface of the end effector is electrically conductive.

It is also an object of the invention to provide a substantially non-conductive end effector with an electrically conductive reinforcing core or skeleton.

It is another object of the invention to provide methods of manufacturing selectively conductive end effectors.

It is a further object of the invention to provide means for electrically coupling a selected conductive surface of an end effector to an electrical source.

It is yet another object of the invention to provide means for electrically coupling selected conductive surfaces of two end effector members to an electrical source for bipolar cautery.

It is still another object of the invention to provide a non-metallic end effector having a strength enhancing metal spine.

In accord with these objects which will be discussed in detail below, the present invention includes an endoscopic surgical instrument having a tube with a push rod or wire axially movable therein and coupled at its proximal end to an actuator. An end effector is coupled to the push rod or wire at the distal end of the tube through a clevis so that axial movement of the push rod is translated to rotational or pivotal movement of the end effector. The end effector is formed of both conductive material and non-conductive material; the non-conductive material surrounding all of the conductive material but for a selected electrode surface and a selected surface for coupling with an electrical source.

Preferred aspects of the invention include insert molding a conductive metal in a non-conductive ceramic or plastic end effector. Alternatively, the end effector may be formed by injection molding a non-conductive end effector and plating conductive surfaces onto it. Another preferred method of forming the end effector is by casting a conductive end effector and coating it with an insulating polymer or other insulating material. Preferred conductive surfaces include a single conductive point electrode rising from or flush with the surface of an otherwise non-conductive end effector or a linear electrode surface on an otherwise non-conductive end effector. Alternatively, the conductive surface may be a plurality of defined conductive electrode surfaces on an otherwise non-conductive end effector. It is also preferred that means be provided for electrically coupling the conductive surface of the end effector to an electrical source through the tube and/or the push rod of the endoscopic instrument. When both the tube and the push rod are separately coupled to different poles of an electrical source, as with a bipolar arrangement, means for electrically insulating the push rod, clevis, tube and end effectors from each other are also provided.

In accord with other aspects of the invention, different end effectors for endoscopic instruments are provided which use metal cores or spines as reinforcement for plastic, or which use metal cutting edges as part of a plastic end effector. The end effectors are not necessarily used in conjunction with a cautery application.

Additional objects and advantages of the invention will become apparent to those skilled in the art upon reference to the detailed description taken in conjunction with the provided figures.

BRIEF DESCRIPTION OF THE DRAWING

FIG. 2b is a perspective view of the end effector of FIG. 2a;

FIGS. 9a and 9b are side elevation views in partial cross section of an endoscopic tool with bipolar selective cautery end effectors;

FIG. 10b is a transparent perspective view of the arthroscopic end effector of FIG. 10a.

DETAILED DESCRIPTION OF THE PREFERRED EMBODIMENTS

Figure 1A:
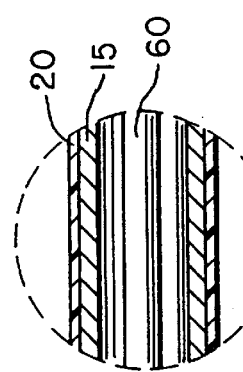
FIG. 1a is an enlarged detail of the tube of the instrument of FIG. 1.
Figure 1:
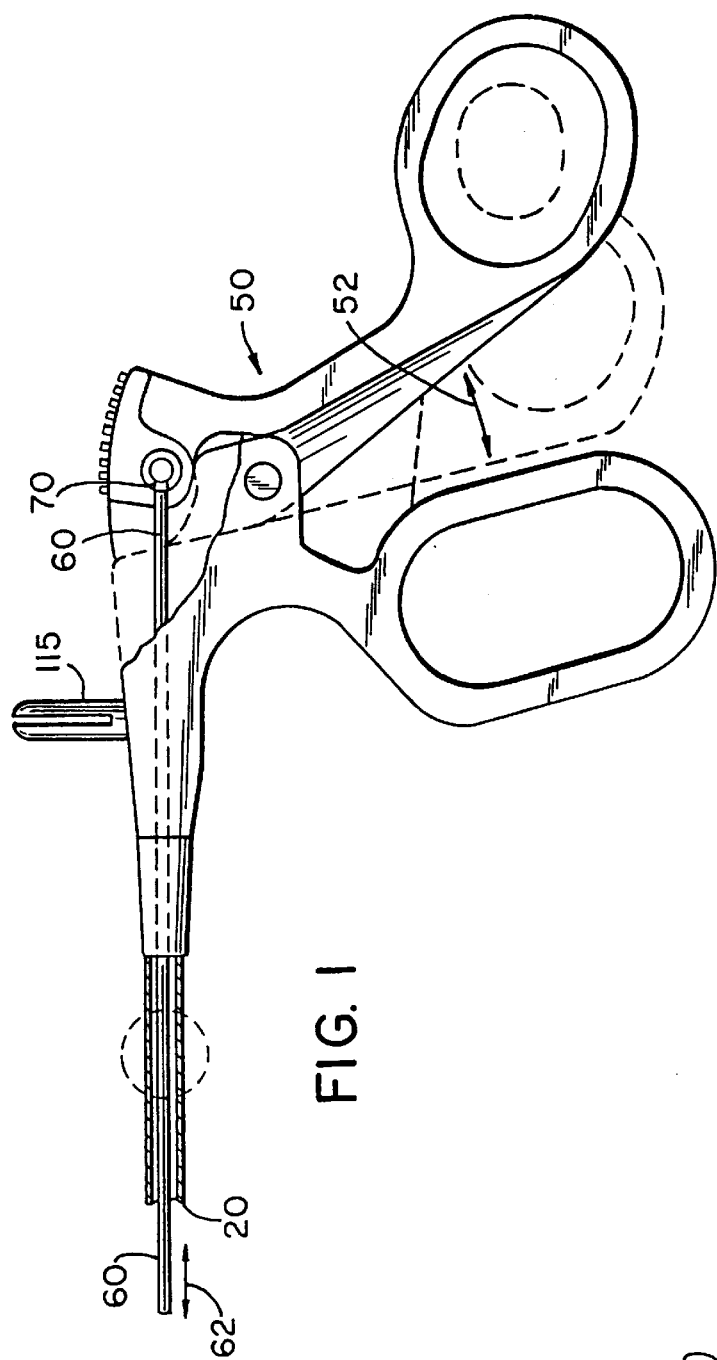
FIG. 1 is a side elevation in partial cross section of the proximal end of an endoscopic instrument with an electrical connection to the tube.
Figure 1B:
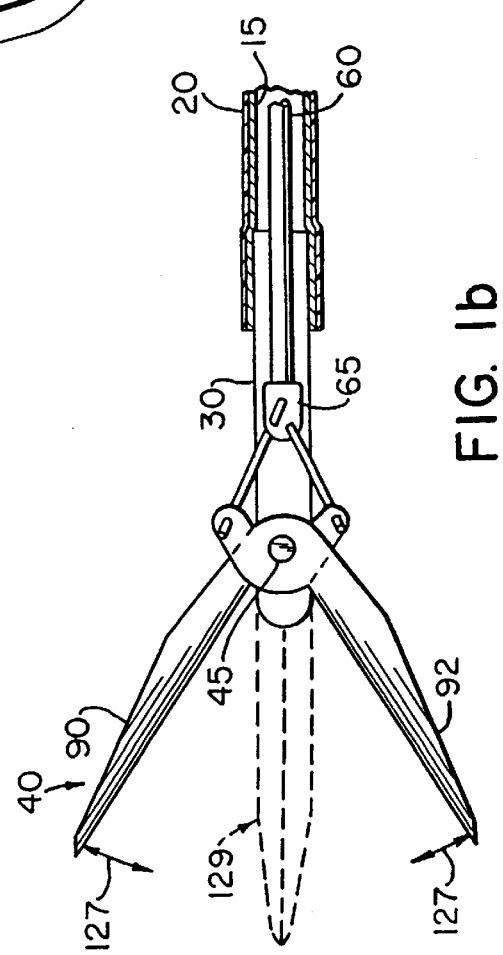
FIG. 1b is a side elevation view of the distal end of the instrument of FIG. 1.

An endoscopic surgical instrument is shown in FIGS. 1, 1a and 1b and generally includes a metal (e.g., aluminum) tube 15 surrounded by a peripheral insulating shrink wrap layer of plastic 20, a clevis 30, end effectors 40, actuating means 50, and a push rod 60. The clevis 30 is usually a separately formed aluminum piece which fixedly engages aluminum tube 15 and also engages the end effectors 40 which pivotally engage clevis 30 at pivot pin 45. End effectors 40 generally includes two members 90, 92 at least one of which is pivotally engaged to clevis 30. When both members are pivotally engaged, the instrument is said to be "double acting" whereas when only one of the members 90, 92 is pivotally engaged, the instrument is said to be "single acting". The push rod 60, which is also usually formed of aluminum or stainless steel, is engaged at its distal end 65 to the end effector 40 and is connected its proximal end 70 to a manually operable actuating means 50. In use, the endoscopic instrument is inserted with the members 90, 92 of the end effector 40 in the closed position 129, through a trocar tube into a body incision. The members 90, 92 can be opened and closed, as indicated by arrows 127, by reciprocal motion, as indicated by arrows 62, of push rod 60 which results from operation, as indicated by arrows 52, of the manual actuating means 50.

The endoscopic instrument shown in FIG. 1 includes an electrical connector 115 which couples an electrical source to the tube 15 and thus to the clevis 30 and the end effector 40 for monopolar cautery.

Figure 2:
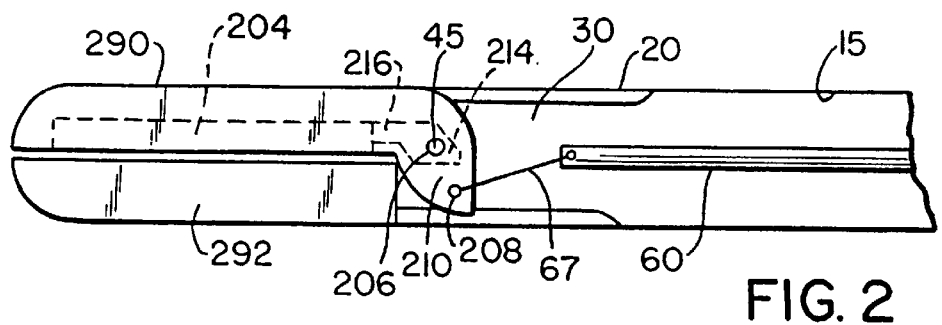
FIG. 2 is a side elevation schematic view of the distal end of an endoscopic instrument with single action selective cautery end effector.

Referring now to FIG. 2, an end effector 290 according to the invention is shown mounted on a clevis 30 by a clevis pin 45 at the distal end of an endoscopic instrument such as the one shown in FIG. 1. The end effector shown in FIG. 2 is a "single acting" end effector since movement of push rod 60 effects rotation of end effector member 290 about clevis pin 45 while a stationary member 292 is fixedly coupled to the clevis 30 or tube 15.

Figure 2A:
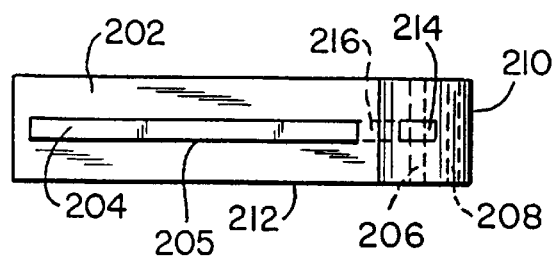
FIG. 2a is a bottom plan view of the selective cautery end effector of FIG. 2.
Figure 2B:
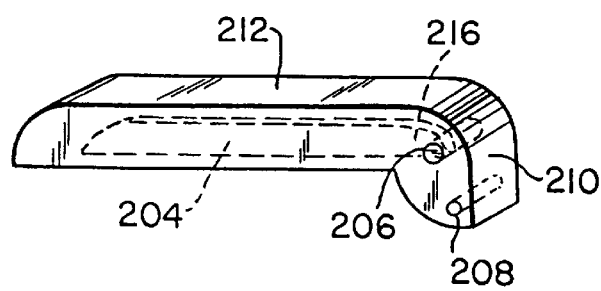

Turning to FIGS. 2a and 2b with reference to FIG. 2, end effector 290 generally includes a distal portion 212 and a proximal portion 210 with a pivot bore 206 therebetween. The end effector is mounted on the clevis 30 by a clevis pin 45 which passes through the pivot bore 206 of the end effector 290 and engages the clevis 30. The proximal portion 210 of the end effector 290 includes a second "actuation" bore 208 which receives either a link 67 which couples the end effector to the push rod 60 or the push rod itself so that axial movement of the push rod 60 through the tube 15 causes rotation of the end effector about the clevis pin 45. The distal portion 212 of the end effector generally includes a working surface 202 which in this embodiment is a gripping surface. In accord with the invention, the end effector 290 is constructed of non-conductive material such as molded plastic or non-conductive ceramic. In order to provide a selected conductive surface within the working surface 202 and to strengthen the end effector 290, a metal spine 204 is insert molded in the non-conductive material of which the end effector is made. In this embodiment, the conductive spine 204 occupies part of the distal portion 212 of the end effector, extending along a relatively thin surface 205 within the working surface 202 of the end effector, penetrating within the body of the end effector to a portion 216 which is totally insulated by the non-conductive body of the end effector and emerging at 214 to communicate with the pivot bore 206. As will be appreciated by those skilled in the art, the selected narrow conductive surface 205 of end effector 290 is electrically coupled to the tube 15 via the conductive clevis pin 45 which extends through the pivot bore 206, and via the conductive clevis 30 which couples the tube and the pin. When an electrical source is coupled to the tube 15 as shown in prior art FIG. 1, end effector 290 becomes an electrocautery electrode with a very well defined conductive surface 205. During electrocautery operations, surrounding tissues are protected from the conductive surface 205 by the otherwise non-conductive body of the end effector 290. In order to insulate the conductive clevis 30 from surrounding tissues, the plastic layer 20 covering tube 15 is preferably extended to cover the clevis 30 as shown in FIG. 2.

Figure 3:
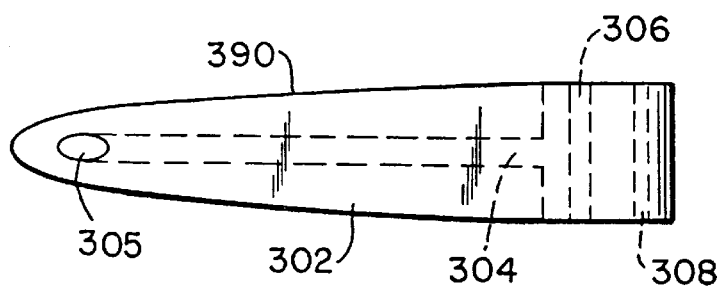
FIG. 3 is a top plan view of an embodiment of a double action selective cautery end effector.
Figure 3A:
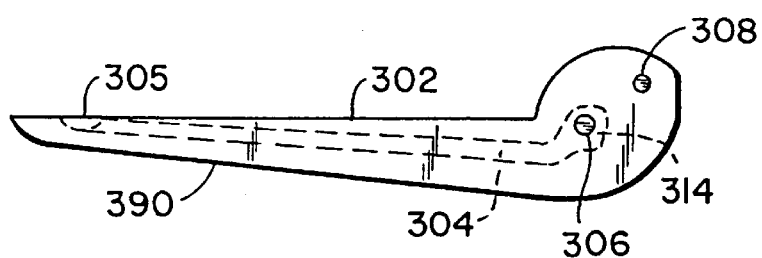
FIG. 3a is a side elevation view of the end effector of FIG. 3.
Figure 3B:
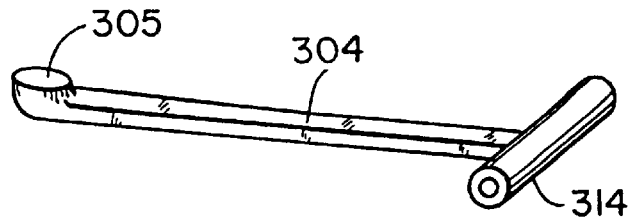
FIG. 3b is a perspective view of a conductive core or skeleton used to insert mold the end effector of FIG. 3.

The method of insert molding a conductive spine or skeleton in a non-conductive end effector can be used to produce a variety of single acting or double acting instruments. FIGS. 3 through 6b show but a few embodiments of the invention using this method of insert molding. FIGS. 3, 3a and 3b show a gripper end effector 390 with a very small conductive spot electrode 305 formed on its working surface 302 by an insert molded conductive spine 304. As with the embodiment of FIG. 2, this spine 304 extends into the body of the end effector to create an electrical coupling at 314 through the pivot bore 306 of the end effector 390. Thus, the spot electrode 305 formed on the working surface 302 of the end effector 390 receives its electrical connection through the clevis and tube as described above.

Figure 4:
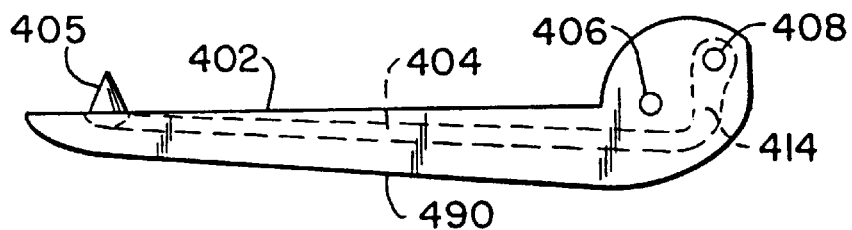
FIG. 4 is a view similar to FIG. 3b but of another embodiment of selective cautery end effector.
Figure 4A:
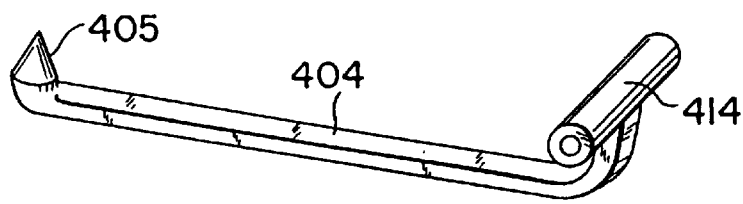
FIG. 4a is a perspective view of a conductive core or skeleton used to insert mold the end effector of FIG. 4.

FIGS. 4 and 4a show another embodiment of end effector 490 having a pointed electrode 405 rising from the working surface 402. In this embodiment, inserted spine 404 extends into the body of the end effector to a portion 414 for an electrical coupling through actuation bore 408 of the end effector. With end effector 490, an electrical source is coupled to the push rod of an endoscopic instrument as described in detail below with reference to FIGS. 9a and 9b. It should be noted that in this embodiment, the pivot bore 406 is non-conductive and insulated from the spine 404 by the non-conductive body of the end effector 490. similarly, in the end effectors 290, 390 described above, the actuation bores 208, 308 are non-conductive and insulated from the pivot bores 206, 306 by the non-conductive body of the end effector. As described in detail below with reference to FIGS. 9a and 9b, using one end effector member with an electrode surface coupled to the pivot bore and another end effector member with an electrode surface coupled to the actuation bore makes endoscopic bipolar selective cautery possible.

Figure 5:
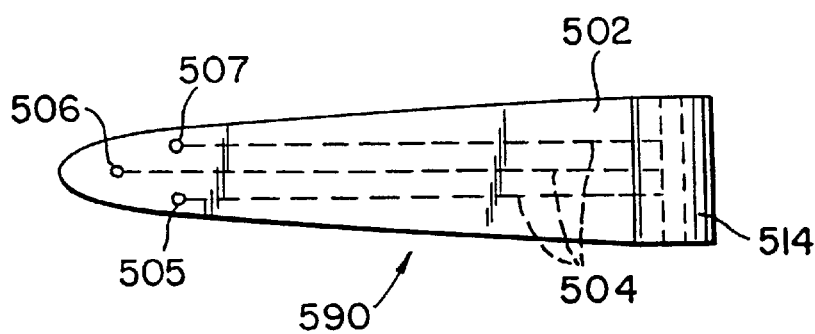
FIG. 5 is a top plan view of yet another embodiment of selective cautery end effector.
Figure 5A:
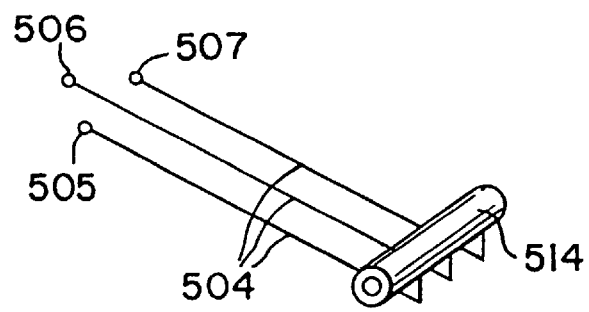
FIG. 5a is a perspective view of a conductive core or skeleton used to insert mold the end effector of FIG. 5.

The inserted conductive spine may be more than just a single element "spine" or "core". FIGS. 5 and 5a show an embodiment of end effector 590 having three surface point electrodes 505, 506, 507 on its working surface 502. These three electrodes are formed by inserting a fork-like skeleton 504 in the mold for the end effector 590. The fork-like skeleton 504 has three tines which extend from the surface points through the body of the otherwise non-conductive end effector to a collar 514 which may be aligned with either the pivot bore or the actuator bore of the end effector. It will be appreciated by those skilled in the art that the metal tines not only serve to provide a selective cautery function, but also act to strengthen the overall structure of the end effector.

Figure 6:
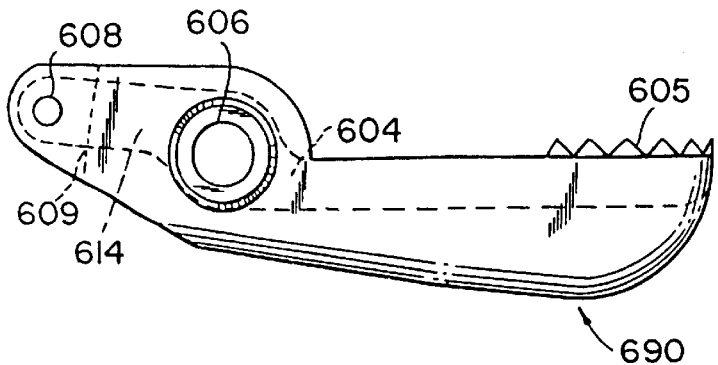
FIG. 6 is a side elevation view of a biopsy forceps jaw end effector having a conductive skeleton insert molded in a non-conductive body.
Figure 6A:
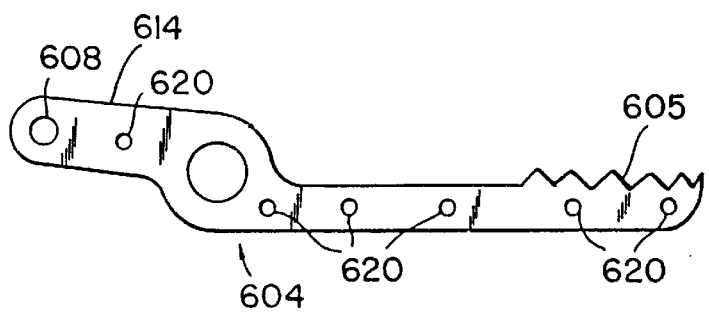
FIG. 6a is a side elevation view of the conductive skeleton of the end effector of FIG. 6.
Figure 6B:
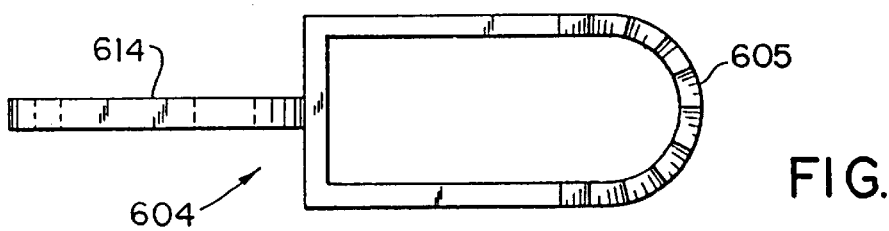
FIG. 6b is a top plan view of the skeleton of FIG. 6.

FIGS. 6, 6a, and 6b show a more elaborate skeleton 604 used to construct a biopsy forceps jaw end effector 690 with conductive teeth 605. In this embodiment, conductive skeleton insert 604 is formed by casting, stamping, or by photochemical milling or machining and is preferably provided with a number of fixation (staking) holes 620. The skeleton is used as an insert for an insert-type injection mold which is filled with plastic. While the skeleton 604 is inserted in the mold, the non-conductive plastic or ceramic material flows through these staking holes 620 to anchor the skeleton and strengthen the end effector. The proximal end 614 of the skeleton may enter the pivot bore 606 or the actuator bore 608 as shown. Moreover, the skeleton may exit the end effector shell at the proximal end as indicated by dotted line 609 whereby the actuator bore 608 in the proximal end 614 of the skeleton is available for an electrically conductive coupling with a push rod.

Figure 7:
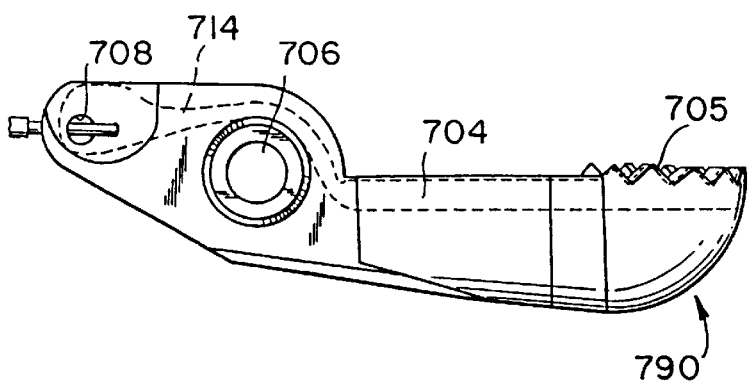
FIG. 7 is a side elevation view of a biopsy forceps jaw end effector of injection molded plastic whose teeth are rendered conductive by an external conductive trace.

In addition to insert molding, a selectively conductive end effector can be formed by injection molding with subsequent selective plating. FIG. 7 shows an injection molded ceramic (e.g. alumina, zirconia, etc.) biopsy forceps jaw 790 with plated traces 714, 704, 705 for electrical conductivity in the teeth and at the proximal connection 708 to a push rod or other actuator. The plated traces are provided on the ceramic surface or in the ceramic and may be applied by sputtering or by other suitable procedures.

Figure 8:
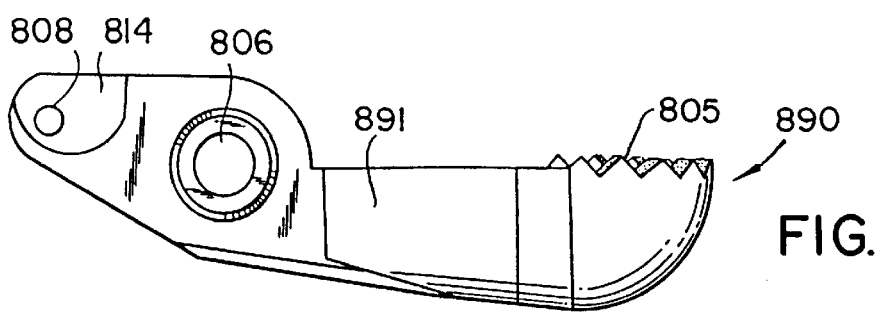
FIG. 8 is a side elevation view of a biopsy forceps jaw end effector cast in metal and selectively coated with an insulating polymer.

Besides molding, cast end effectors can be made selectively conductive by coating. FIG. 8 shows a cast biopsy forceps jaw 890 coated with a very thin highly insulating polymer 891 such as PARYLENE manufactured by Union Carbide. The teeth 805 and proximal connection 814 are uncoated and thus conductive. These conductive portions can be masked before coating the jaw or can be ground or polished to remove portions of the coating after the jaw is coated. The PARYLENE is preferably deposited evenly on the jaw surfaces by applying it in a tumbling or other process in a vacuum at room temperature with the teeth 805 and proximal connection 814 masked before coating. It will also be appreciated that removal of the polymer from the proximal connection can be effected by drilling hole 808 after coating to provide an uninsulated surface within hole 808.

As mentioned above, any of the embodiments of the selectively conductive end effectors can be made to electrically couple with either the clevis pin or the push rod, and a double acting bipolar selective cautery end effector can be constructed by making one of the end effector elements electrically couple with the tube and the other couple with the push rod (provided the tube and push rod are electrically isolated from each other). FIGS. 9a and 9b show a bipolar selective cautery endoscopic instrument where one pole is coupled through the tube 15 and the other through the push rod 60. As mentioned above, with reference to FIG. 1, it is known to couple an electrical source to the tube 15 as with connector 115 shown in both FIG. 1 and FIG. 9a. FIG. 9a also shows, however, an electrical connection through connector 160 which couples with the proximal end 70 of the push rod 60. With both of these connections, it is possible to provide bipolar cautery at the distal end of the instrument shown in FIG. 9b.

Figure 10A:
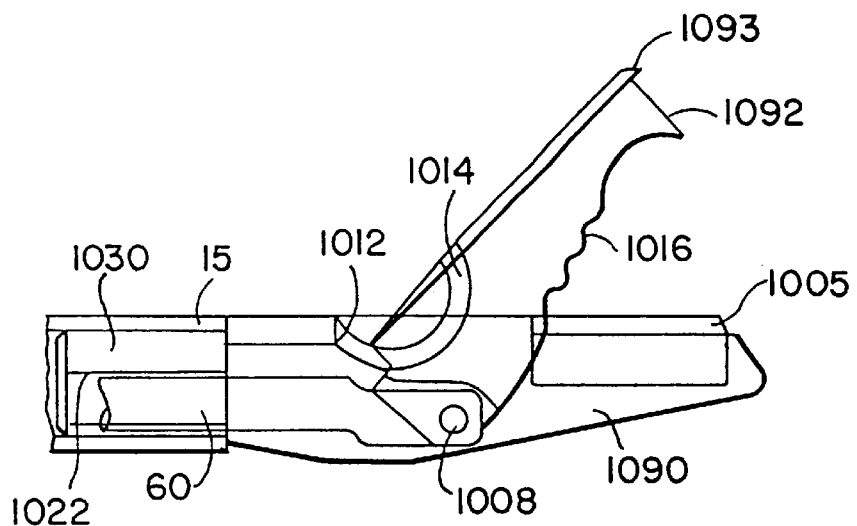
FIG. 10a is a transparent side elevation view of an insert molded arthroscopic end effector with a conductive razor blade insert.
Figure 10B:
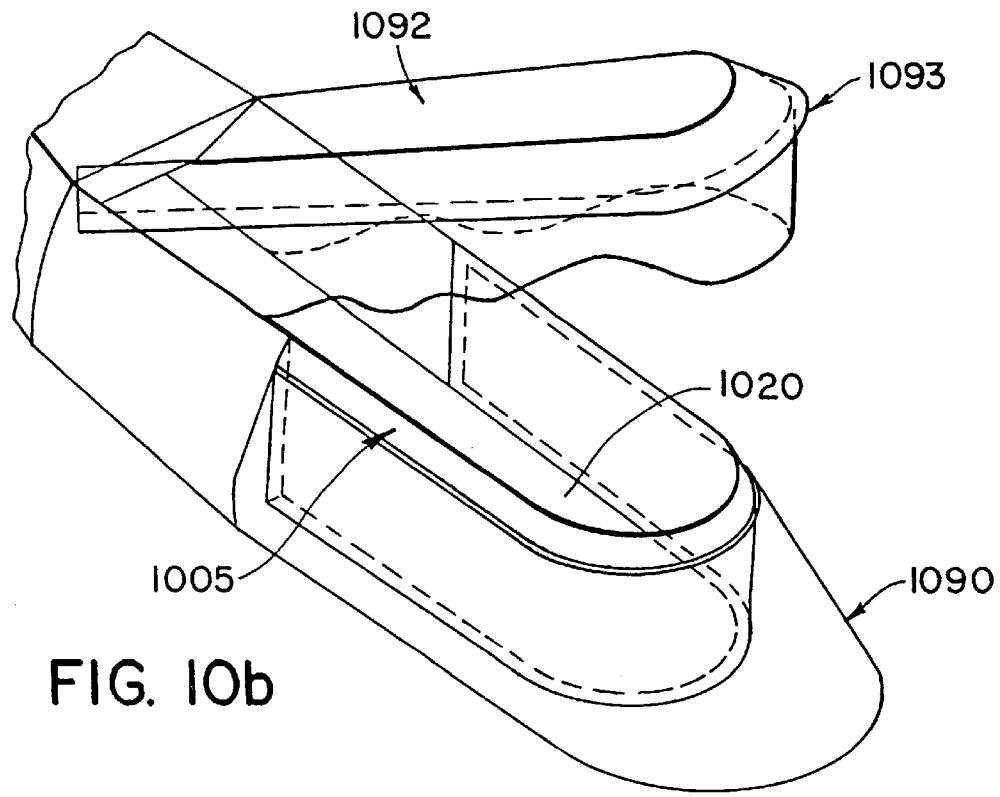

FIG. 9b shows a conductive clevis 30 with a conductive clevis pin 45 electrically coupling the pivot bore 906 of an end effector member 90. End effector member 90 is constructed in a manner similar to the end effector 390 shown in FIG. 3a insofar as the selected conductive portion on the working surface of the end effector is electrically coupled with the pivot bore while the rest of the end effector is non-conductive. In this manner, the electrical pole coupled to connector 115 in FIG. 9a is coupled through the tube 15, the clevis 30, and the clevis pin 45 to the selected conductive portion of end effector 90 via the pivot bore 906. FIG. 9b also shows push rod 60 electrically insulated from clevis 30 by a non-conductive lining 23 on the interior surface of clevis 30. Push rod 60 is coupled to the actuation bores 908, 909 of end effector members 90 and 92 by conductive links 67. End effector member 92 is constructed in a manner similar to the end effector 490 in FIG. 4 insofar as the selected conductive portion on the working surface of the end effector is electrically coupled with the actuation bore while the rest of the end effector is non-conductive. In this manner, the electrical pole coupled to connector 160 in FIG. 9a is coupled through the push rod 60 and the conductive links 67 to the selected conductive portion of end effector member 92 via the actuation bore 909. Because both end effectors are non-conductive but for their selected conductive surface and proximal connection to either the pivot bore or the actuation bore as described above, the conductive link 67 makes no electrical coupling to end effector member 90 and the conductive clevis 30 and clevis pin 45 make no electrical coupling to end effector member 92. FIGS. 10a and 10b show a surgical punch end effector having a stationary jaw 1090 and a movable jaw 1092. The stationary jaw has a shank portion 1030 which fits lockingly inside tube 15 and which is provided with a throughbore 1022 for receiving a push rod 60. The movable jaw is pivotally attached to the stationary jaw by mating surfaces 1012, 1014 and is linked to the distal end of the push rod 60 by a pin 1008. The stationary jaw 1090 is provided with an opening 1020 into which the movable jaw 1092 pivots. In this way the stationary jaw functions as a die and the movable jaw as a punch for cutting through tissue. In accord with the invention, the end effector of FIG.s 10a and 10b is constructed of injection molded plastic or ceramic with a preformed and ground razor blade 1005 insert molded into the opening 1020 of the stationary jaw 1090. The movable jaw 1092 is provided with an overlapping rim 1093 which covers the blade 1005 when the jaws are closed. The razor blade 1005 is typically conductive, while the remainder of the end effector is non-conductive. If desired, the conductive blade 1005 can be electrically coupled to the tube 15 in any of the ways discussed above.

There have been described and illustrated herein several embodiments of a selectively conductive end effector member and means for electrically coupling end effector members to an electrical source. While particular embodiments of the invention have been described, it is not intended that the invention be limited thereto, as it is intended that the invention be as broad in scope as the art will allow and that the specification be read likewise. Thus, while particular types of end effectors, namely grippers, and arthroscopic and biopsy jaws, have been disclosed, it will be appreciated that other types of end effectors can embody the invention. It is possible, therefore to use the methods and materials disclosed herein to create other types of end effectors such as cutters, dissectors, scissors, and the like. Also, while specific clevis, push rod and actuation means have been shown, it will be recognized that the selective cautery end effectors of the invention could be used with other kinds of endoscopic instruments having somewhat different clevis and actuation mechanisms. Thus, while the selective cautery end effector members have been disclosed as having pivot bores and actuation bores, it will be appreciated that other arrangements can be utilized. Likewise, it will be understood that stationary end effector members without pivot or actuation bores can be constructed according to the invention, for example for use in bipolar single action end effectors.

It will further be appreciated by those skilled in the art that while particular conductive and non-conductive materials have been disclosed, other materials could be used as well. In addition, while non-conductive end effector members with conductive cores have been shown for the purpose of selective cautery, it will also be recognized that a metallic core in a non-metallic end effector member strengthens the member and allows the construction of less expensive non-metallic end effectors which may be useful without cautery. It will therefore be appreciated by those skilled in the art that yet other modifications could be made to the provided invention without deviating from its spirit and scope as so claimed.

We claim:

1. A method of manufacturing an end effector for an endoscopic surgical instrument having an actuation means, comprising:

forming a metallic skeleton by a process chosen from casting, stamping or photochemically milling; and molding a non-conductive body around said metallic skeleton, said non-conductive body having a proximal end with means for coupling to the actuation means, and a distal end with means for cutting, gripping, clamping, or otherwise contacting tissue.

2. A method according to claim 1, wherein:

in said molding step, said metallic skeleton is located in a manner such that a distal end of said metallic skeleton extends to a surface portion of said non-conductive body.

3. A method according to claim 1, wherein:

said metallic skeleton is formed with at least one pivot hole.

4. A method according to claim 1, wherein:

said metallic skeleton is formed with at least one hole which comprises said means for coupling to the actuation means.

5. A method according to claim 1, wherein:

said metallic skeleton is formed with at least one fixation hole through which said non-conductive body extends.

6. A method according to claim 3, wherein:

said metallic skeleton is formed with at least one hole which comprises said means for coupling to the actuation means, and said metallic skeleton is formed with at least one fixation hole through which said non-conductive body extends.

7. A method according to claim 1, wherein:

said molding step comprises insert molding said metallic skeleton in said non-conductive body.

8. A method according to claim 1, wherein:

said metallic skeleton comprises a metal core having a plurality of tines.

9. A method of manufacturing an end effector for an endoscopic surgical instrument having an actuation means and a clevis means, comprising:

casting a conductive body according to an investment casting process, said conductive body having a proximal end, and a surface portion adjacent where said end effector grasps, clamps cuts, or otherwise contacts a tissue, said cast conductive body including means for coupling said end effector to the actuation means and means for coupling said end effector to the clevis means;

coating said cast conductive body with a non-conductive coating except for at least one selected first location on said surface portion on said conductive body, and except for at least one selected second location located at at least one of said means for coupling said end effector to the clevis means and said means for coupling said end effector to the actuation means; and masking said cast conductive body with masking means at said at least one selected first location and at said at least one selected second location prior to said step of coating, and removing said masking means after said step of coating.

* * * * *